US012797220B2

(12) United States Patent
Dyer et al.

(10) Patent No.: US 12,797,220 B2
(45) Date of Patent: Nov. 17, 2026

(54) ORTHOTIC DEVICE

(71) Applicants: Karin Dyer, Philadelphia, PA (US); Summer Lee, San Diego, CA (US); Jessica Inacio, Sewickley, PA (US); Isha Gadgil, Bensalem, PA (US); Rachel Hagani, Woodbridge, CT (US)

(72) Inventors: Karin Dyer, Philadelphia, PA (US); Summer Lee, San Diego, CA (US); Jessica Inacio, Sewickley, PA (US); Isha Gadgil, Bensalem, PA (US); Rachel Hagani, Woodbridge, CT (US)

( * ) Notice: Subject to any disclaimer, the term of this patent is extended or adjusted under 35 U.S.C. 154(b) by 405 days.

(21) Appl. No.: 18/326,556

(22) Filed: May 31, 2023

(65) Prior Publication Data

US 2024/0398596 A1 Dec. 5, 2024

(51) Int. Cl.
*A61F 5/01* (2006.01)

(52) U.S. Cl.
CPC .................................. *A61F 5/0118* (2013.01)

(58) Field of Classification Search
CPC .... A61F 5/0118; A61F 5/013; A61F 5/05866; A61F 5/05875; A61F 5/10; A61H 1/0288
USPC ...................................................... 602/21, 22
See application file for complete search history.

(56) References Cited

U.S. PATENT DOCUMENTS

| | | | | |
|---|---|---|---|---|
| 4,875,469 | A * | 10/1989 | Brook | A61H 1/0288 601/40 |
| 5,527,244 | A * | 6/1996 | Waller | A63B 23/16 482/49 |
| 5,538,488 | A * | 7/1996 | Villepigue | A63B 21/023 601/40 |
| 7,601,130 | B2 * | 10/2009 | Farrell | A63B 23/16 602/22 |
| 7,740,561 | B2 * | 6/2010 | Kupferman | A63B 21/4025 482/148 |
| 9,463,109 | B2 * | 10/2016 | Kilbey | A61F 5/0118 |

(Continued)

FOREIGN PATENT DOCUMENTS

| | | | | |
|---|---|---|---|---|
| DE | 102015113827 A1 * | 2/2017 | | A61F 5/0127 |
| EP | 4461273 A1 * | 11/2024 | | A61F 5/0118 |

OTHER PUBLICATIONS

Jurkat, Jorg, Orthosis for the reciprocal coupling of two body joints, Aug. 20, 2015 (Year: 2015).*

*Primary Examiner* — Alireza Nia
*Assistant Examiner* — Robin Han
(74) *Attorney, Agent, or Firm* — Kilpatrick Townsend & Stockton LLP; Charles W. Gray; Micah C. Cheng

(57) ABSTRACT

The present disclosure provides orthotic devices wearable on a user's hand and wrist. In one example, an orthotic device includes a brace and multiple finger extension assemblies. The brace includes a first portion and a second portion connected to the first portion and arranged to respectively cover a top portion and a bottom portion of the user's hand and wrist, a closure mechanism configured to form a closure between the first portion and the second portion, and a thumb support configured to prevent thumb flexion of the user's thumb. Each of the plurality of the finger extension assemblies includes a tensioning member, at least one finger band movably connected to the tensioning member and wearable on a phalange of the finger, and a tension control member configured to apply and control a tension on the finger band to cause extension of the finger to a desired position.

19 Claims, 10 Drawing Sheets

(56) References Cited

U.S. PATENT DOCUMENTS

| | | | | |
|---|---|---|---|---|
| 10,603,202 | B1 * | 3/2020 | Fried | A61F 5/0118 |
| 11,179,263 | B1 * | 11/2021 | Cofer | A61F 5/013 |
| 2005/0273030 | A1 * | 12/2005 | Koby | A61F 5/0118 602/21 |
| 2010/0234182 | A1 * | 9/2010 | Hoffman | A61F 5/013 482/8 |
| 2012/0289876 | A1 * | 11/2012 | Hegland | A61F 5/0118 602/22 |
| 2016/0361179 | A1 * | 12/2016 | Mateus Dias Quinaz | A61F 2/72 |
| 2020/0329794 | A1 * | 10/2020 | Luplow | A41D 19/0024 |
| 2023/0390093 | A1 * | 12/2023 | Wheeler | A61F 5/0118 |

* cited by examiner

ORTHOTIC DEVICE

BACKGROUND OF THE DISCLOSURE

Orthotic devices have been widely used in the treatment, prevention, or support of the temporarily or permanently incapacitated arm, wrist, and hand, whether partially or fully impaired. For example, cerebral palsy (CP), a congenital disorder that affects movement, muscle tone, and posture, may cause permanent incapacitation of the arm, wrist, and hand. CP is caused by abnormal brain development, usually before birth, so symptoms tend to develop at a young age. Temporary incapacitation may be caused by repetitive motion injuries resulting from overuse of arm, wrist, and hand, and traumatic injuries such as bone fractures and lacerations.

There are challenges with the existing orthotic devices. Their complex and bulky nature may interfere with a patient's freedom of movement and comfort. Further, existing devices are often difficult to customize to meet the needs of a particular patient. Also, the ability to provide both flexible support and flexion/extension control is not achieved simultaneously in a single device.

BRIEF SUMMARY OF THE DISCLOSURE

In accordance with some embodiments of the present disclosure, an orthotic device is provided. In one example, an orthotic device includes a brace and a plurality of finger extension assemblies. The brace is wearable on a user's hand and wrist and can include a first portion, a second portion connected to the first portion along a center line substantially aligned with the user's forearm, a closure mechanism, and a thumb support. The first portion is arranged to cover a top portion of the user's hand and wrist, the second portion is arranged to cover a bottom portion of the user's hand and wrist, the closure mechanism is arranged and configured to form a closure between the first portion and the second portion and to secure the brace worn on the user's hand and wrist, and the thumb support is configured to receive and accommodate a portion of the user's thumb and to prevent thumb flexion of the user's thumb. The finger extension assemblies respectively correspond to the user's fingers, and each finger extension assembly further includes: a tensioning member, at least one finger band wearable on a phalange of the finger, and a tension control member. The tensioning member anchored on an exterior surface of the brace and extends from a proximal stopper to a distal stopper. The finger band is wearable on a phalange of the finger and adapted to receive the phalange. The finger band further includes: a tightening element configured to fasten the finger band to the phalange, and a connecting element configured to movably connect the finger band to the tensioning member proximate the distal stopper. The tension control member is attached to the tensioning member proximate the proximal stopper ad is configured to apply and control a tension on the at least one finger band connected to the tensioning member to cause extension of the finger to a desired position.

In accordance with some embodiments of the present disclosure, a kit is provided. The kit includes components used for assembly of an orthotic device described herein. In one example, the kit includes: a brace wearable on a user's hand and wrist, at least one cord extending from a proximal end and a distal end, a cord lock, and at least one anchor. The brace further includes a first portion, a second portion connected to the first portion along a center line substantially aligned with the user's forearm, a closure mechanism, and a thumb support. The first portion is arranged to cover a top portion of the user's hand and wrist, the second portion is arranged to cover a bottom portion of the user's hand and wrist, the closure mechanism is arranged and configured to form a closure between the first portion and the second portion and to secure the brace worn on the user's hand and wrist, and the thumb support is configured to receive and accommodate a portion of the user's thumb and to prevent thumb flexion of the user's thumb. The cord lock is attachable to the cord proximate the proximal end and is configured to apply and control a tension on the finger band connected to the cord lock. The anchor is mountable on an exterior surface of the first portion of the brace and is configured to anchor the cord onto the brace.

In accordance with some embodiments of the present disclosure, a method for making an orthotic device is provided. In one example, a method includes: providing a brace according to the present disclosure, mounting a plurality of anchors to the exterior surface of the brace, forming a plurality of finger extension assemblies, and anchoring the plurality of finger extension assemblies on the brace through use of the anchors. Forming a plurality of finger extension assemblies may include connecting at least one finger band to a tensioning member and connecting the tensioning member to a tension control member. The method may further include inserting a support pad in a pouch on an interior surface of the brace.

In accordance with some embodiments of the present disclosure, a method for using an orthotic device is provided. In one example, a method includes: providing an orthotic device described herein, causing the brace of the orthotic device to be worn by a user and securing the brace on the user's hand and wrist, placing one of the finger bands on a phalange of the user's finger and securing the finger band on the phalange, applying a tension on the tensioning member of the finger extension assembly, and adjusting/controlling the tension to extend the finger to a desired or optimal position relative to the user's hand.

BRIEF DESCRIPTION OF THE DRAWINGS

A further understanding of various embodiments may be realized by reference to the following figures. In the appended figures, similar components or features may have the same reference label. Further, various components of the same type may be distinguished by following the reference label with a dash and a second label that distinguishes among the similar components. If only the first reference label is used in the specification, the description is applicable to any one of the similar components having the same first reference label irrespective of the second reference label.

DETAILED DESCRIPTION OF THE DISCLOSURE

Figure 1:
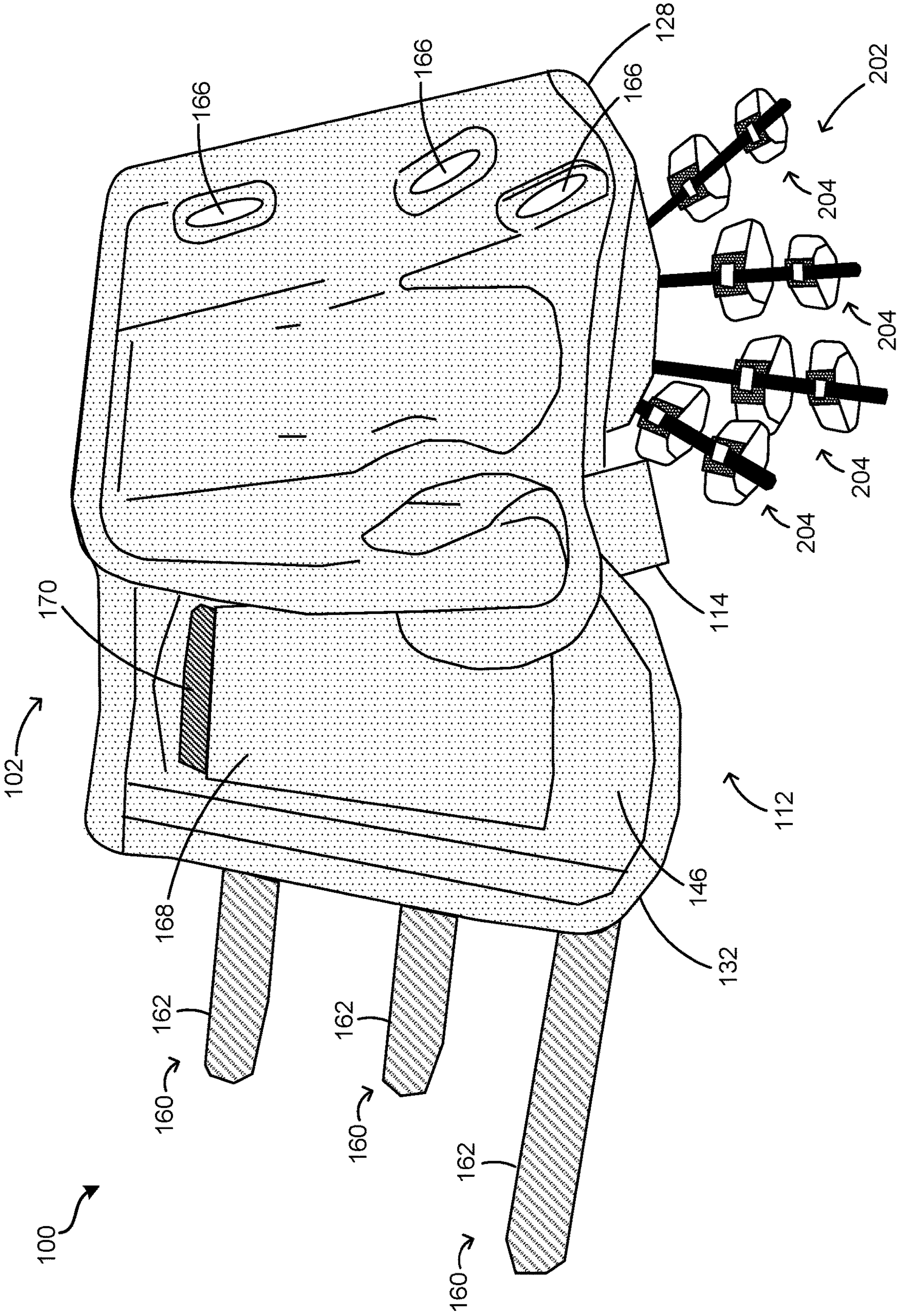
FIG. 1 schematically illustrates a perspective view of an orthotic device according to various embodiments.

The present disclosure provides orthotic devices and methods for the treatment, prevention, or support of the temporarily or permanently incapacitated arm, wrist, and hand of a user. The present orthotic device includes both a flexible and wearable brace that supports hand and wrist and a finger extension mechanism that promotes finger extension.

One insight provided by the present disclosure is that the present orthotic device can be an off-the-shelf, lightweight device to integrate individualized bracing and physical therapy for children between the ages of 5 and 10 with mild to moderate spastic cerebral palsy (CP). CP is the most common motor disability in children, with the overall birth prevalence being approximately 2 in 1,000 live births in the United States. Leaving CP symptoms in children untreated is not an option. Although there is no cure to date for CP, therapies to manage muscle control and pain symptoms associated with the disease are crucial to ensuring the patient can perform essential daily tasks and live as comfortably as possible. Current therapies include occupational therapy, assistive technology, medications, and surgery. Each option is accompanied by a significant financial burden and demands significant time and energy from the patient and the patient's family in order to prove effective. Thus, there is an overwhelming need for more affordable and effective treatment options, particularly for improved efficacy and longer-term treatment at a reduced cost for the patient with CP. In addition, conventional orthotic devices are often complex in design and tend to be bulky and heavy, which can interfere with the performance of some daily tasks. These conventional orthotic devices can become tiring and painful to wear for an extended period of time. Lastly, CP patients spend countless hours each week in occupational therapy, which proves to be a significant inconvenience for both the patient and the parent.

The present orthotic device provides improvements in many aspects. The present orthotic device provides optimal positioning of the wrist and fingers out of the typical flexed position that is associated with spastic CP. The present orthotic device utilizes variable tension bands to deliver personalized treatment to the patient and work to build up muscle fibers in the fingers and promote heightened muscle relaxation and control. The present orthotic device serves to combat musculoskeletal deformities during childhood and allows for easier performance of common grasp and release tasks.

More generally, the present orthotic device can be used to relax the muscle tone of the wrist flexors and promote finger extension. Relaxation of the muscle tone can be achieved by positioning the wrist in an optimal position for function through use of the brace. Positioning the wrist out of flexion also allows the finger flexors to act more volitionally to grasp. Secondly, the finger extension mechanism and thumb support of the orthotic device act to assist in finger and thumb extension. Overall, the present device helps to position and assist with balancing the multiple joints in the wrist and hand for optimal functioning of the finger flexors and extensors. This ultimately serves to promote heightened muscle relaxation in the wrist and hand and enables the easier performance of daily tasks.

In addition, the present orthotic device serves to integrate occupational therapy into an orthotic device to take advantage of everyday activities as a means of promoting muscle relaxation and control. By incorporating the device into a patient's home exercise program from their therapist, the present orthotic device can promote overlap between the completion of daily functional living tasks and therapeutic exercises. The present orthotic device can enable CP patients to see quicker results without having to spend more hours in physical or occupational therapy.

Figure 2:
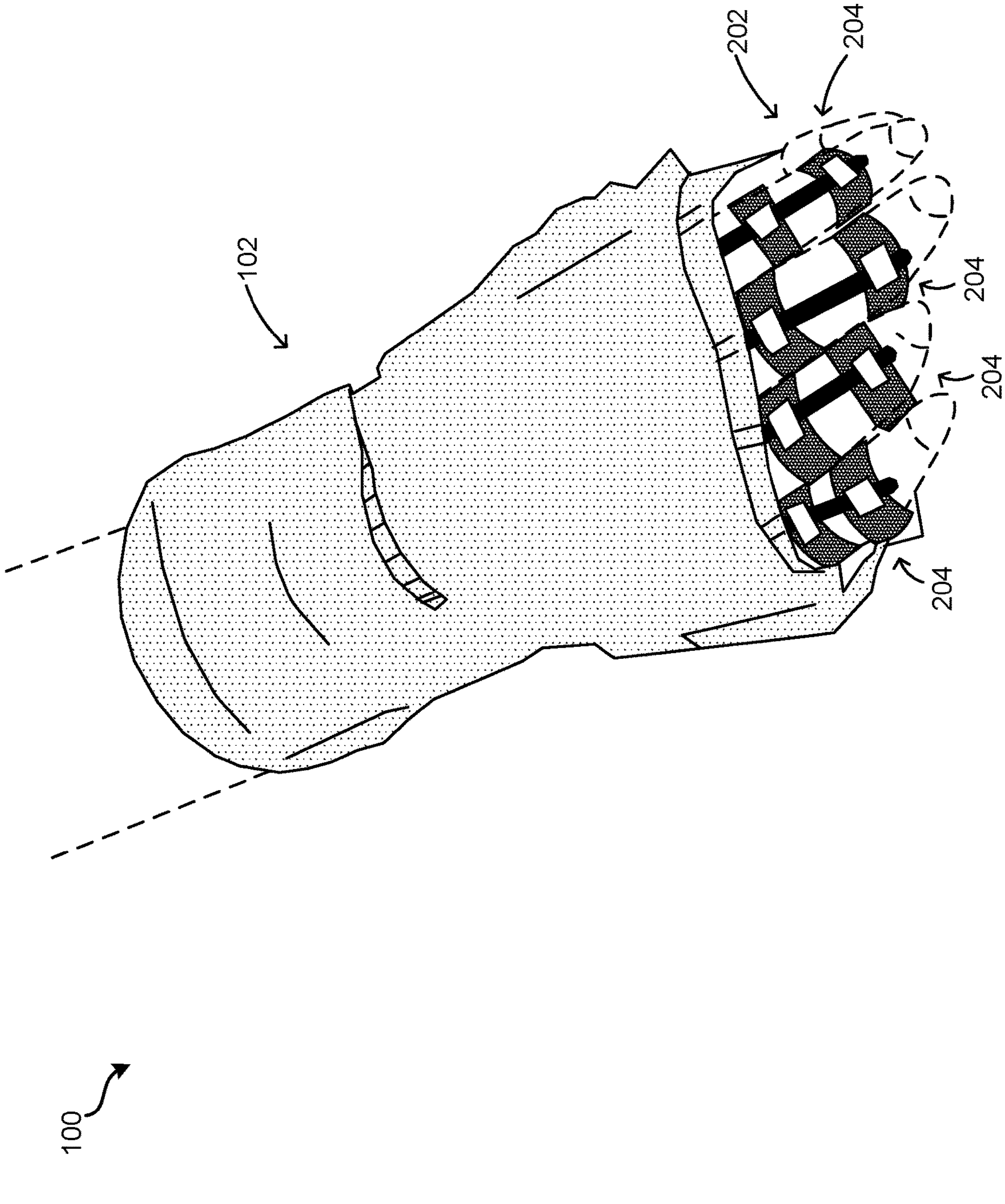
FIG. 2 schematically illustrates a perspective view of an orthotic device worn by a user according to various embodiments.
Figure 3A:
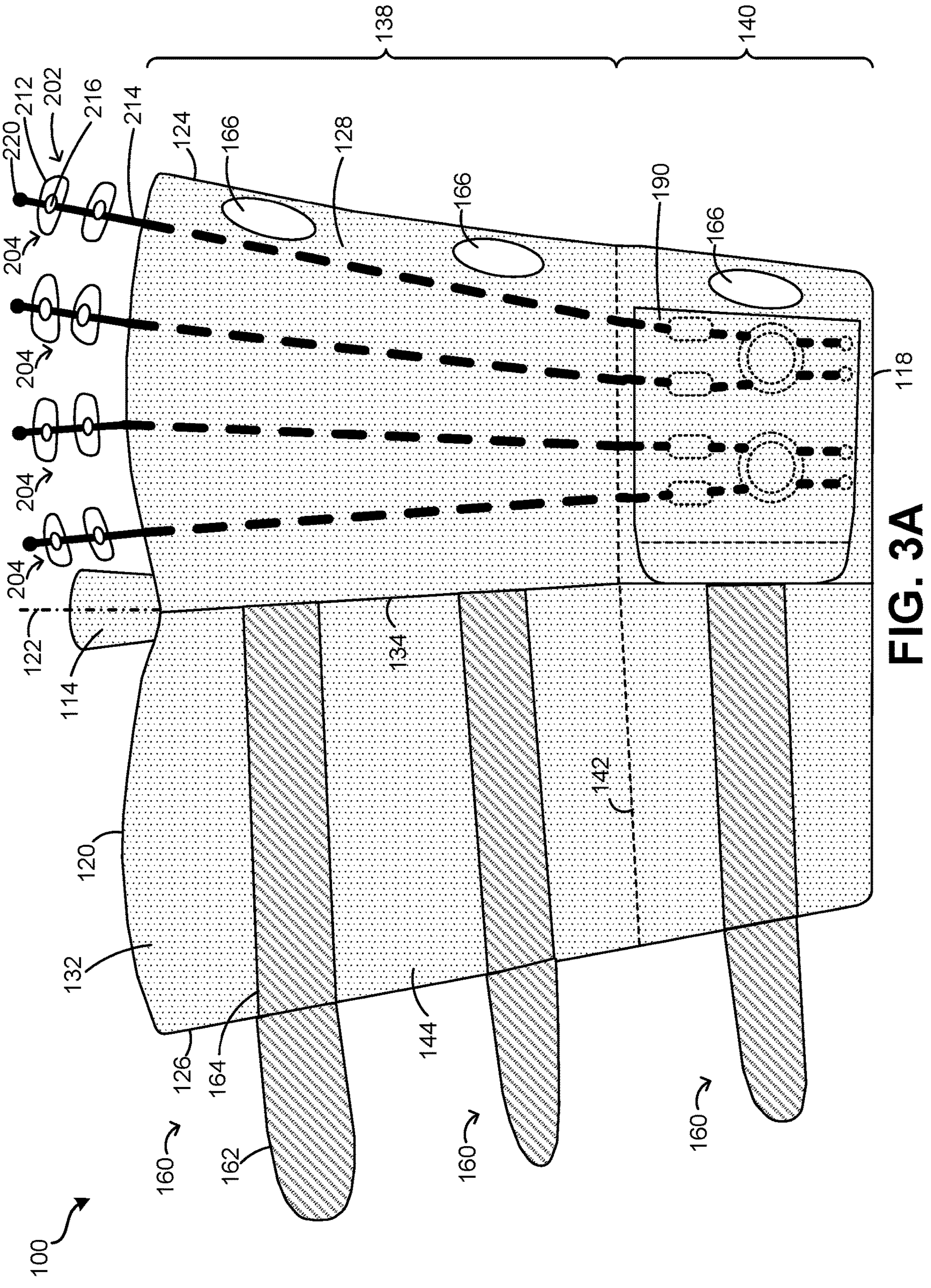
FIG. 3A schematically illustrates a top plan view of the orthotic device according to various embodiments.
Figure 3B:
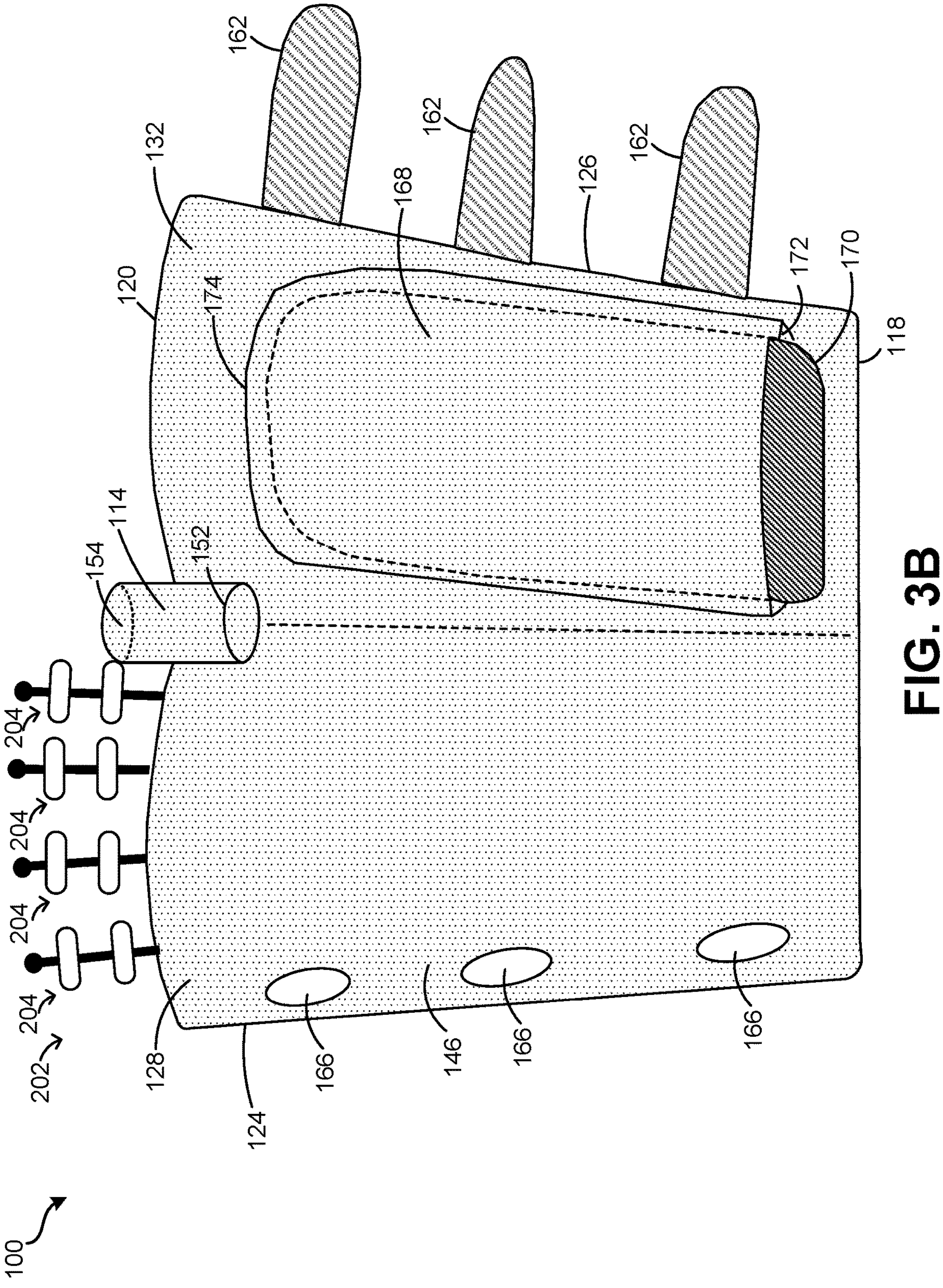
FIG. 3B schematically illustrates a bottom plan view of an orthotic device according to various embodiments.
Figure 4A:
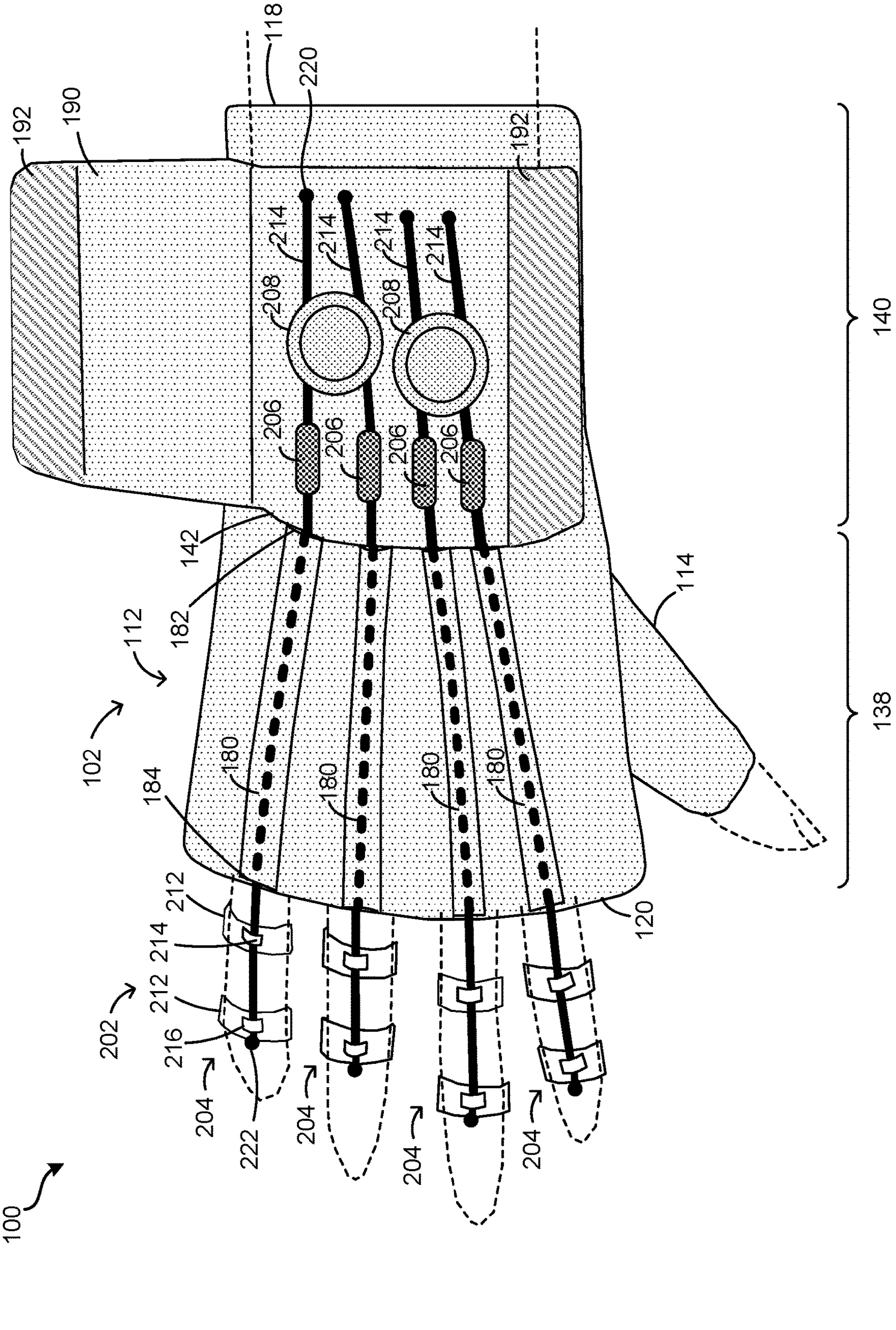
FIG. 4A schematically illustrates a top plan view of the orthotic device worn by a user and extending from the forearm to the hand of the user according to various embodiments.
Figure 4B:
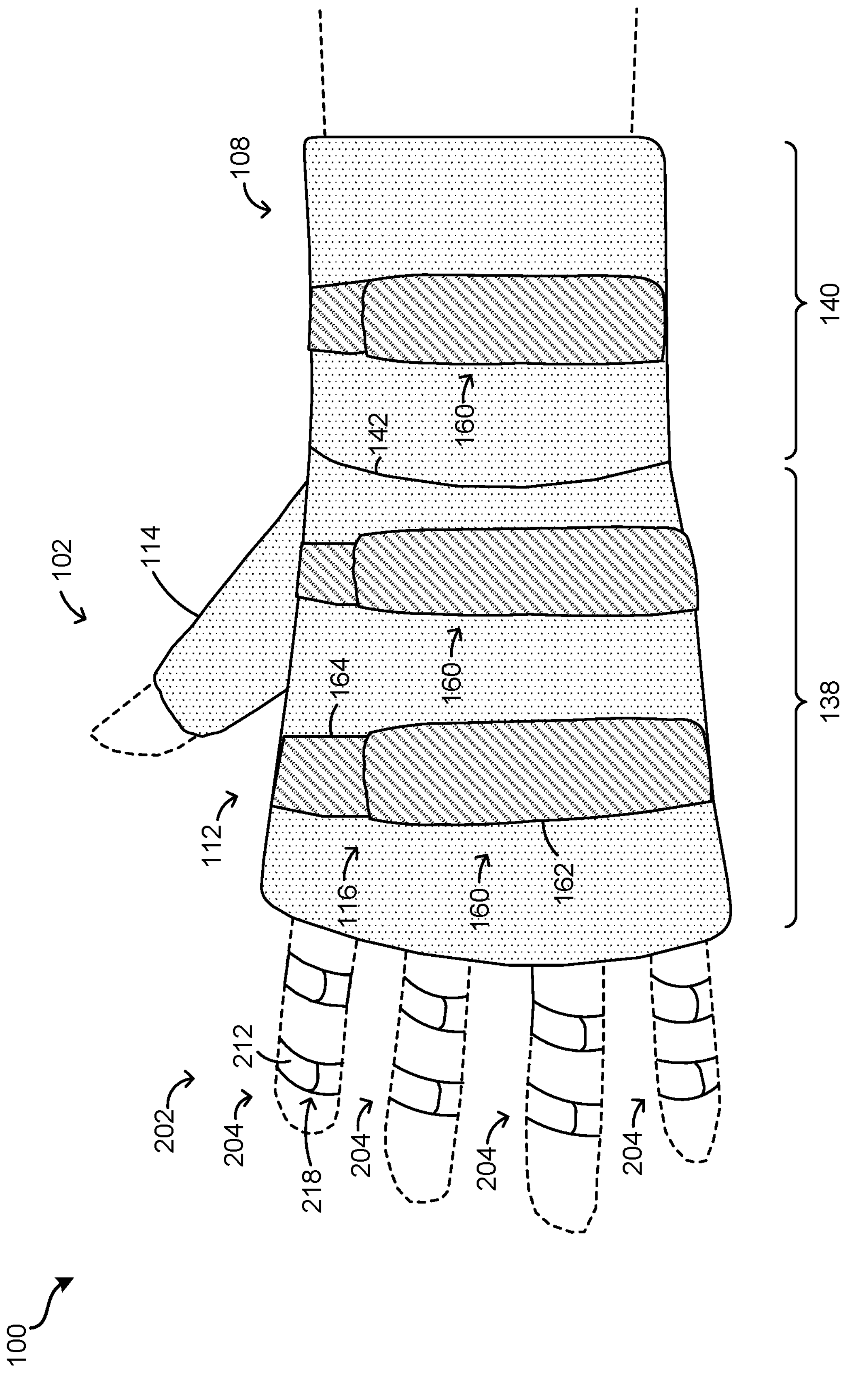
FIG. 4B schematically illustrates a bottom plan view of an orthotic device worn by a user and extending from the forearm to the hand of the user according to various embodiments.

FIGS. 1-2, 3A-3B, and 4A-4B illustrate an example of an orthotic device 100 according to various embodiments of the present disclosure. FIG. 1 is a perspective plan view of the orthotic device 100. FIG. 2 is a perspective plan view of the orthotic device 100 worn by a user. FIG. 3A is a top plan view of the orthotic device 100. FIG. 3B is a bottom plan view of the orthotic device 100. FIG. 4A is a top plan view illustrating the orthotic device 100 worn by a user. FIG. 4B is a bottom plan view illustrating the orthotic device 100 worn by the user. The orthotic device 100 can be used to relax muscle tone of the wrist flexors, promote finger extension, protect and prevent hyperextension and hyperflexion movements of the metacarpal, carpal, radius and ulna regions, and provide normal pitch and yaw movements of a user. In the illustrated example, the orthotic device 100 includes, among other components, a brace 102 and a finger extension mechanism 202.

The brace 102 is configured to wrap around, cover, and support a majority of the hand, wrist, and/or a portion of the forearm adjacent to the wrist of the user. The brace 102 may be made of a soft, moisture-wicking, and washable neoprene fabric. The brace 102 includes, among other components, a major body 112, a thumb support 114, and a closure mechanism 116. The major body 112 extends from a proximal edge 118 to a distal edge 120, along a longitudinal axis 122 aligned with the forearm of the user. The major body 112 extends laterally from a first side 124 to a second side 126 across the longitudinal direction. The major body 112 further includes a first portion 128 and a second portion 132 jointed at a center line 134 aligned with the longitudinal axis 122. The first portion 128 extends laterally from the center line 134 to the first side 124. Likewise, the second portion 132 extends laterally from the center line 134 to the second side 126. The major body 112 is foldable along the center line 134, such that when the orthotic device 100 is worn by a user, the first portion 128 and the second portion 132 may rotate about the center line 134 to allow the first side 124 and the second side 126 to approach to each other, such that the first portion 128 and the second portion 132 may be arranged and positioned to wrap around and cover the hand, wrist, and forearm of the user. In this arrangement, the first portion 128 covers the top surface of the hand, wrist, and forearm, and the second portion 132 covers the bottom surface of the hand, wrist, and forearm. The distal edge 120 may be aligned or substantially aligned with the base of the four fingers of the user (i.e., the forefinger, the middle finger, the ring finger, and the little finger) when the orthotic device 100 is worn by the user, such that the fingers may extend out of the distal edge 120 of the major body 112 when in use.

The major body 112 may include a hand region 138 and a wrist region 140 separated by an imaginary line 142. The line 142 is in proximity to the juncture of the user's wrist and palm of the hand. The hand region 138 may cover a majority of the hand (i.e., the metacarpals and carpals regions); the wrist region 140 may cover a majority of the writ and a portion of the forearm (i.e., the radius and ulna region). The major body 112 has an exterior surface 144 and an interior surface 146. When the orthotic device 100 is worn by the user, the exterior surface 144 is exposed while the interior surface 146 is in contact with the skin of the user.

The thumb support 114 is attached to and integrated with the major body 112. The thumb support 114 has a tubular structure configured to receive and accommodate the thumb of the user when the orthotic device 100 is worn by the user. The thumb support 114 extends from a proximate opening 152 that opens to the interior surface 146 of the major body to a distal opening 154 in a direction aligned with the thumb. In some embodiments, the thumb support 114 has a splint-like structure and configuration. The thumb support 114 may be made of a semi-rigid material or semi-rigid in nature to keep the thumb immobilized and prevent thumb flexion when the thumb is placed in the thumb support 114.

The closure mechanism 116 is configured to reversibly form a closure that connects the first portion 128 and the second portion 132 when the orthotic device 100 is worn by the user. In some embodiments, the closure mechanism 116 includes one or more releasable fasteners 160. For example, one or more releasable fasteners 160 may be placed in the hand region 138, and one or more releasable fasteners 160 may be placed in the wrist region 140. In some embodiments, a total number of the releasable fasteners 160 is at least 3.

In the example illustrated in FIG. 3, the releasable fastener 160 is of a hook and loop type (e.g., a Velcro fastener) and includes a first bonding member 162 (i.e., a hook or loop strap) and a second bonding member 164 (i.e., a hook or loop pad) corresponding to the first bonding member 162. The first bonding member 162 may be attached to the second portion 132 and extend out of the second side 126, and the second bonding member 164 may be mounted on the exterior surface 144 of the second portion 132. When the major body 112 wraps around and covers the hand, wrist, and forearm of the user, the first bonding member 162 (i.e., the strap) may be arranged to pass through a corresponding aperture 166 located in the first portion 128 proximate to the first side 124 to form a closure between the first portion 128 and the second portion 132. The first bonding member 162 is removably bonded to the corresponding second bonding member 164 through hook and loop fastening to further secure the closure of the major body 112.

In some embodiments, the first bonding member 162 may be attached to the first portion 128 and extend from the first side 124, and the second bonding member 164 may be mounted on the exterior surface 144 of the second portion 132. The first bonding member 162 may be directly bonded to the corresponding second bonding member 164 through hook and loop fastening without the need to go through an aperture of the first portion 128, when the major body 112 wraps around and covers the hand, wrist, and forearm of the user.

It is noted that the releasable fasteners 160 is not limited to the hook and loop type fastener, and other closure mechanisms such as adhesive, pins, screws, buttons, nuts, bolts, adjustable zippers, snaps, threaded strings, and the like are also within the scope of the present disclosure.

In some embodiments, the major body 112 further includes a pouch 168 arranged and configured to receive and accommodate a removable support pad 170. The pouch 168 may be formed and located on the interior surface 146 of the second portion 132. In the illustrated example, the pouch 168 extends from an open end 172 proximate the proximal edge to a closed end 174 proximate to the distal edge 120 in the longitudinal direction. The support pad 170 can be removably inserted into the pouch 168 from the open end 172 and remain therein in use. The support pad 170 is made of a semi-rigid and flexible material such as aluminum. When the orthotic device 100 is worn by the user, the support pad 170 inserted in the pouch 168 lies against the bottom side of the hand, wrist, and forearm. The support pad 170 provides additional support to the wrist and allows the wrist to be secured out of flexion in an optimal position for functionality. Due to both the flexibility and semi-rigidity, the support pad 170 can bend to conform to a desired angle between the hand and the forearm of the user when the orthotic device 100 is in use.

The finger extension mechanism 202 is configured to promote finger extension, tighten the user's fingers, pull the user's fingers to a spread position, and facilitate the alignment of the fingers and hand. The finger extension mechanism 202 includes a plurality of finger extension assemblies 204. In the illustrated example, the finger extension mechanism 202 includes four finger extension assemblies 204 respectively corresponding to the forefinger, middle finger, ring finger, and little finger, an anchor 206, and a tension control member 208.

Each of the four finger extension assemblies 204 is operable to control the extension of the corresponding finger. Typically, each finger has three phalanges, namely a proximal phalange, an intermediate phalange, and a distal phalange. In the illustrated example, each finger extension assembly 204 further includes at least one finger band 212 and a tensioning member 214. The number of the finger bands 212 may vary depending on design requirements. In some embodiments, each finger extension assembly 204 includes two finger bands 212 adapted to circumferentially wrap and secure the proximal phalange and the intermediate phalange of each finger, respectively. Alternatively, each finger extension assembly 204 may contain only one finger band or more than two finger bands. The width of the finger bands (i.e., the dimension of the finger band in the direction of the finger) may also vary depending on the size of the phalange and other design requirements. For example, each finger extension assembly 204 may include one relatively wider finger band that can wrap around and secure both the proximal phalange and the intermediate phalange of each finger. Alternatively, each finger extension assembly 204 may include at least two relatively shorter finger bands that can wrap around and secure each one of the phalanges of the finger.

Each finger band 212 further includes a connecting element 216 and a tightening element 218. The connecting element 216 is configured to connect the finger band 212 to the tensioning member 214. The tightening element 218 is arranged and configured to circumferentially tighten the finger band 212 when the finger band 212 is placed on and wraps around the phalange, such that the position of the finger band 212 relative to the phalange can be secured through tightening. The tightening element 218 can operate reversibly and loosen the finger band to release the finger when not in use.

FIGS. 5A-5B illustrate an example of the finger band 500 according to various embodiments. The finger band 500 is a representative example of the finger band 212 shown in FIG. 1. In the illustrated example, the finger band 500 includes a rigid portion 502 and a flexible portion 504. The rigid portion 502 has a curved shape and is adapted to cover the top portion of the phalange. The rigid portion 502 may be a molded part or print made from smooth resin. The rigid portion 502 has a first end 506, a second end 508, and a connecting member 510 protruding upwardly from the rigid portion. The connecting member 510 is located approximately between the first end 506 and the second end 508 and includes an open channel 512 adapted to allow extension of the tensioning member 214 (e.g., a cord) through the open channel 512. The connecting member 510 and the open channel 512 represent an example of the connecting element 216 of the finger band 212 shown in FIGS. 1-4B. In operation, the tensioning member 214 can be threaded through the open channel 512 of the finger band 500, and more than one finger bands 500 can be connected to the same tensioning member 214 in a similar manner. The finger band 500 may be movable along the tensioning member 214, such that the position of the finger band 500 relative to a specific finger phalange of the finger can be adjusted when the finger band is placed on the finger.

In some embodiments, the rigid portion 502 further includes a plurality of apertures 524 located proximate to the first end 506 and the second end 508. The flexible portion 504 of the finger band 500 may be a soft strip such as fabric or foam strip that is comfortable to the skin of the finger. The flexible portion 504 has a segment 520 that is connected to the first end 506 and the second end 508 of the rigid portion 502 to form a closed loop 514 and is adapted to cover the bottom portion of the phalange. In some embodiments, the flexible portion 504 is tied to the rigid portion through the plurality of apertures 524. For example, the flexible portion 504 may extend through the plurality of apertures 524 and form a closure by tying to the first end 506 and/or the second end 508. The flexible portion 504 may further include a tab 516 connected to the segment 520 and extending out of the closed loop 514. The tab 516 is a representative example of the tightening element 218 of the finger band 212 shown in FIGS. 1-4B. The tab 516 may be manipulated (e.g., pulled or fastened) to shorten the segment 520 of flexible portion 504 between the first end 506 and the second end 508 of the rigid portion 502, and thereby tightening the finger band 500 and secure its position when placed on the finger phalange. In some embodiments, the tab 516 extending out of the closed loop 514 may be bonded to an exterior surface of the closed loop when the finger band 500 is secured on the phalange.

Figure 6:
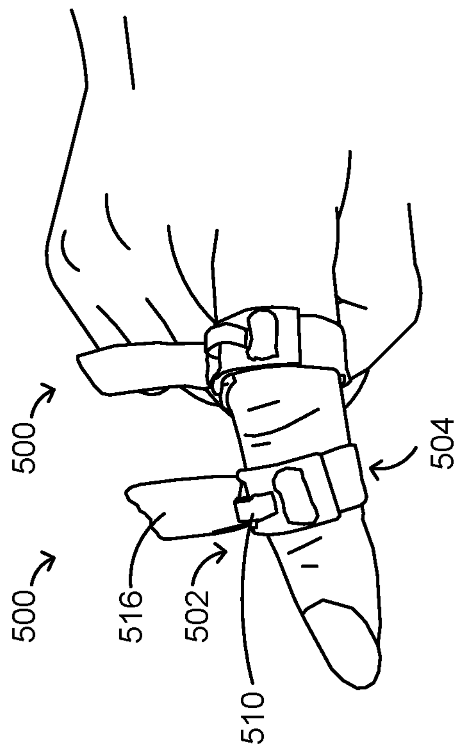
FIG. 6 schematically illustrates a perspective view of multiple finger bands secured on a finger, according to various embodiments.

In the example illustrated in FIG. 6, two finger bands 500 are respectively secured on an intermediate phalange and a proximal phalange. However, the example of FIG. 6 is not intended to be liming, and the number of finger bands 500 for each finger may vary depending on the length of the finger, the width of the finger band, and other consumer needs or design requirements.

Referring back to FIGS. 1-4B, each tensioning member 214 may be made from any substance, including an elastic, plastic, string, strand, fiber, cord, rope, yarn, thread, strap, ribbon, lace, band, cord, spring, or any other rigid or semi-rigid article for connection. In some embodiments, the tensioning member 214 is a cord. A cord used herein may be comprised of multiple filaments or a monofilament. In an exemplary aspect, a cord is an element used in connection with the finger band 212 to secure, tighten, constrict, or otherwise exert a tension force on the finger band 212.

For each finger extension assembly 204, the corresponding tensioning member 214 extends from a proximal stopper 220 attached to a proximate end to a distal stopper 222 attached to a distal end in a direction from the proximal edge 118 to the distal edge 120. In some embodiments, the proximal stopper 220 and the distal stopper 222 may be in a form of a tie. The two finger bands 212 are movably connected to the tensioning member 214 via the connecting element 216 of each finger band 212, respectively. For example, the tensioning member 214 may be threaded through the open channel (e.g., the open channel 512 of FIG. 5) of each finger band to connect and align the two finger bands 212 along the direction of the corresponding finger. The finger bands 212 may be movable along the tensioning member 214.

Figure 5:
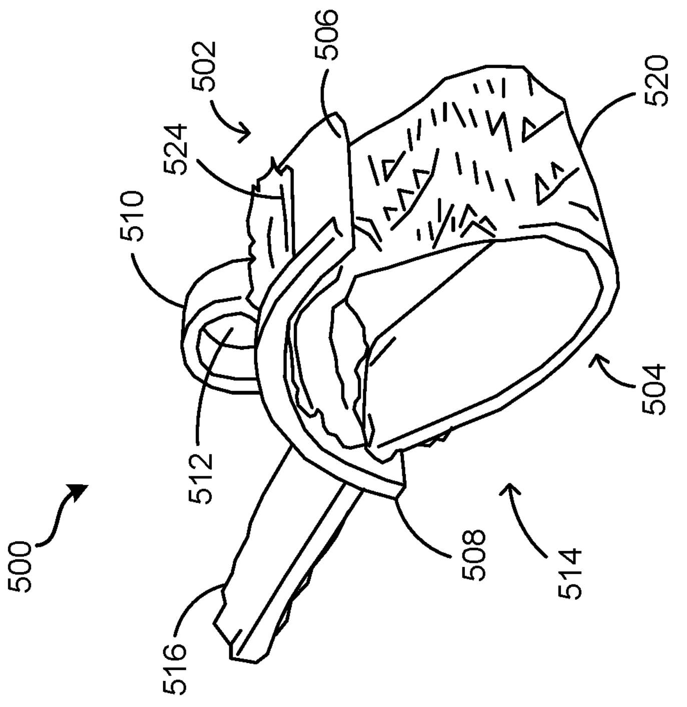
FIG. 5 schematically illustrates a perspective view of an example finger band according to various embodiments.

As an example, when the tensioning member 214 such as a cord is threaded through the opening channel 512 of one or more finger bands 500 as shown in FIGS. 5-6, the finger band 500 is jointed to the cord may be movable along the cord, which allows to adjust the position of the finger band 500 relative to the distal stopper of tensioning member and the relative positions of multiple finger bands 500 on the same tensioning member. One the other hand, the friction between the connecting member 510 of finger band 500 and the tensioning member 214 may be relatively high, such that when the finger band 500 is secured on the phalange, the finger band 500 may not move relative to the tensioning member, but may move along with the tensioning member 214 when a tension is applied on the tensioning member 214. For example, when the tensioning member 214 is pulled in a direction from the distal stopper 222 to the proximal stopper 220, the tensioning member 214 is caused to move in the pulling direction, and the finger band 500 jointed to and carried by the tensioning member 214 also moves along with the tensioning member 214, and thereby causing the extension of the finger from a flexion position (e.g., a curl of bended position inward towards the palm) to an extended position (e.g., straightened or substantially straightened in a direction aligned with the palm).

The tensioning member 214 of each finger extension assembly 204 may be anchored on the major body 112 through the anchor 206. The anchor 206 may be located in the wrist region 140 proximate to the line 142 and mounted on the exterior surface 144 of the major body 112. In some embodiments, the anchor 206 is a molded article having a tubular shape extending between two openings in a direction substantially aligned with the longitudinal axis 122. The anchor 206 is positioned and arranged to allow passage of the tensioning member 214 through the two openings of the anchor 206 and guide the extension of the tensioning member 214. As illustrated, the finger extension mechanism may include four anchors 206 respectively corresponding to the four finger extension assemblies 204. The four anchors 206 may be either separate from each other or integrated in one unit.

In some embodiments, the tensioning member 214 of each finger extension assembly may extend through a vein 180 located between the exterior surface 144 and the interior surface 146 of the major body 112. As illustrated in FIG. 4A, each vein 180 is located in the hand region 138 and extending from a proximal opening 182 at the distal edge 120 to a distal opening 184 at the line 142, in a direction substantially aligned with the corresponding metacarpal of the user's hand. A portion of the tensioning member 214 may extend through the vein 180 from the proximal opening 182 to the distal opening 184. As such, the portion of the tensioning member 214 is buried underneath the exterior surface 144 and protected from exposure by the major body 112.

The tension control member 208 is configured to apply and control a tension force on each finger band 212 connected to the tensioning member 214. The tension force applied on the finger band 212 further causes extension of the corresponding phalange to arrive at a desired or optimal position relative to the hand. However, the fingers of the user may still be permitted movement (e.g., grasp) due to the degree of elasticity of the tensioning member 214. The tension applied on the finger band 212 can be adjusted at any time during operation to adjust the extension level of the finger relative to the hand. In some embodiments, the tension control member 208 may be anchored on the brace 102.

In some embodiments, the tension control member 208 is a cord lock. A "cord lock" as used herein may comprise one or more components, at least some of which are moveable relative to each other for releasably clamping onto a cord to restrict movement of a cord through the cord lock. In some embodiments, a cord lock comprises a spring-loaded barrel and a plunger. The barrel has two openings for the cord (i.e., the tensioning member 214) to enter and exit, and the plunger is located inside the barrel. When the cord is threaded through the barrel and the plunger is pushed into the barrel, it applies pressure to the cord, holding it in place and preventing it from slipping out. To adjust the tension, the plunger is pulled out of the barrel, which releases the pressure on the cord, allowing it to be pulled tighter or loosened. When the desired tension is achieved, the plunger is released and it springs back into place, holding the cord in the new position.

Figure 7:
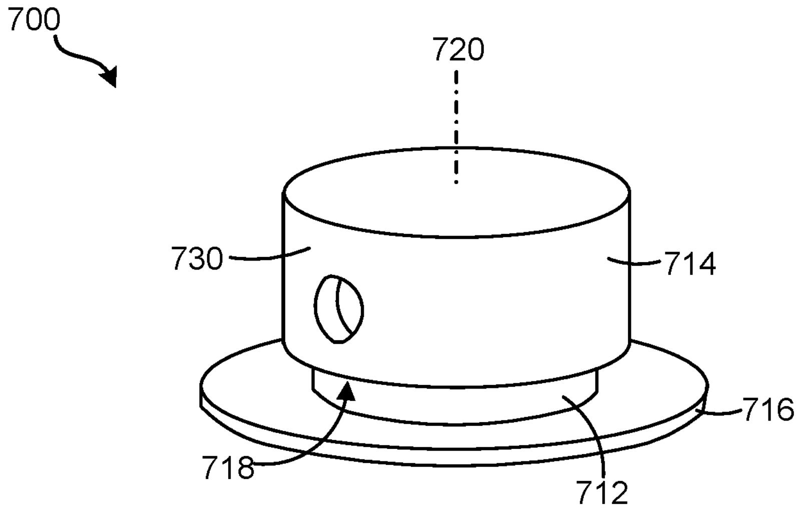
FIG. 7 schematically illustrates a perspective view of a cord lock according to various embodiments.
Figure 8:
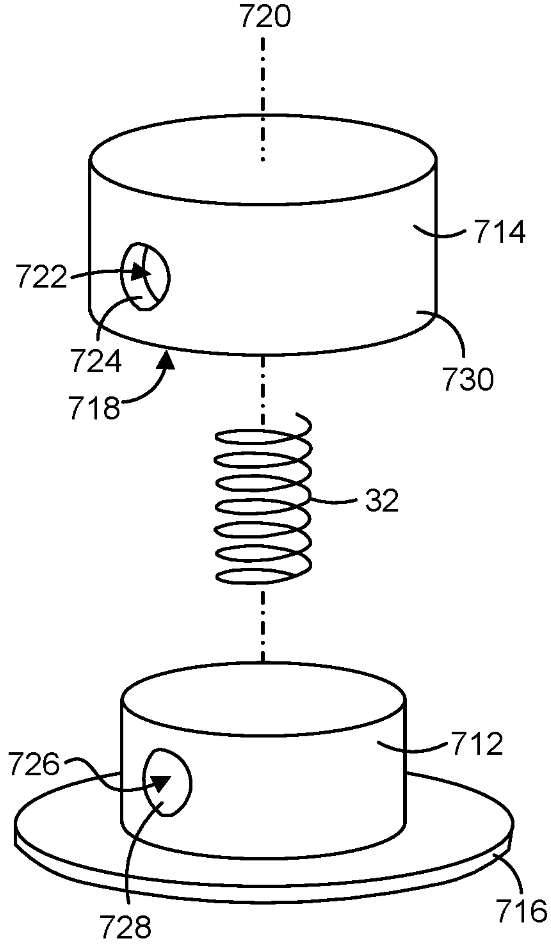
FIG. 8 schematically illustrates an exploded view of the cord lock of FIG. 7 according to various embodiments.

FIGS. 7-8 illustrate an exemplary cord lock 700 according to various embodiments. FIG. 7 is a perspective view of the cord lock 700. FIG. 8 is an exploded view of the cord lock 700 shown in FIG. 7. The cord lock 700 is a representative example of the tension control member 208 shown in FIGS. 1-4B. In the illustrated example, the cord lock 700 includes a plunger 712, a housing 714, and a cap 716 coupled to the plunger 712. The housing 714 includes one or more sidewalls 730 that form a plunger-receiving space 718 within the sidewalls 730, the plunger 712 is at least partially received within the plunger-receiving space 718. The plunger 702 and the housing 714 may be movable relative to each other along an axis 720 of the cord lock 700, allowing components of the cord lock 700 to adjustably clamp onto a cord.

The housing 714 includes at least one opening 722 forming part of a first through-channel 724 extending through the housing 714, and the plunger 712 includes at least one opening 726 forming part of a second through-channel 728 extending through the plunger 712, the first and second through-channels 724, 728 being aligned to allow the tensioning member 214 (i.e., the cord) to pass through the cord lock 700. The housing 714 further includes the one or more sidewalls 730 that form the plunger-receiving space 718 for receiving at least a portion of the plunger 702. A biasing element 732 is coupled between the plunger 712 and the housing 714, and provides a biasing force to actively misalign or de-align the first and second through-channels 724, 728 by biasing the plunger 712 and the housing 714 apart along the axis 720 of the cord lock 10. This misalignment may be used to increase friction/resistance on a cord positioned in the first and second through-channels 724, 728, to restrict movement of the cord therein.

When the plunger 712 is received in the plunger-receiving space 718, and adjustment of a length of cord extending through the cord lock 700 is desired, a force may be applied to the cord lock 700 along the axis 720 of the cord lock 700 to counteract the force from the biasing element 732. As a result, the plunger 712 and the housing 714 move towards each other, which in turn, moves the first and second through-channels 724, 728 towards alignment, reducing restriction on the cord and allowing the length of the cord extending through the cord lock 700 to be adjusted. Upon removal of the force that counteracts the force of the biasing element 732, the plunger 712 and the housing 714 may once again move apart, de-aligning the through-channels 724, 728 and increasing restriction on the cord to help maintain the position of the cord in the through-channels 724, 728.

It should be noted that although it is depicted as cylindrical, the housing 714 and/or the sidewalls 730 of the cord lock 700 may take any shape or configuration (e.g., circular, square, triangular, rectangular, hexagonal, trapezoidal, various prisms, etc.). The sidewall(s) 730 may be one continuous wall or multiple independently defined walls, in various aspects. In some embodiments, the housing 714 and the sidewalls 730 may be configured to allow for moveable engagement with the plunger 712, such as slideable engagement. As such, it is contemplated that components of the cord lock 70 may have a number of configurations, shapes, and sizes while still achieving the aspects provided herein.

It is also noted that the cord lock 700 may be configured to receive, control, and lock multiple cords. For example, each cord lock 700 may be used to control two cords respectively for two finger extension assemblies 204. Each cord associated with the same cord lock 700 may be controlled separately and independently from the other cord. Alternatively, each cord of the finger extension assembly 204 may be controlled by a single cord lock.

In some embodiments, the major body 112 further includes a flap 190 connected to the major body 112. The flap 190 is configured to cover and protect the anchor 206 and the tension control member 208 (i.e., the cord lock) and to prevent tampering with the tension. The flap 190 may include a closure mechanism 192 such as a Velcro releasable fastener that allows the flap to be reversibly bonded to the exterior surface 144.

In some embodiments, the brace 102 further includes a fabric cover (not shown) removably attached to the brace through a releasable fastener such as a Velcro strap. The fabric cover is configured to removably cover a portion or all of the exterior surface of the brace 102 when the brace is worn by the user.

In another aspect, the present disclosure provides a kit for the assembly of an orthotic device described herein. In some embodiments, the kit includes, among other components, the brace 102, a plurality of finger bands 212, a plurality of tensioning members 214, a plurality of the anchors 206, one or more tension control members 208, and optionally a fabric cover. The kit may be provided in a package, and the various components included in the kit may be separate from each other in the package. The kit may further include an instruction describing a method for assembly of the orthotic device 100 using the components included in the kit and a method for using the orthotic device 100 described herein.

Figure 9:
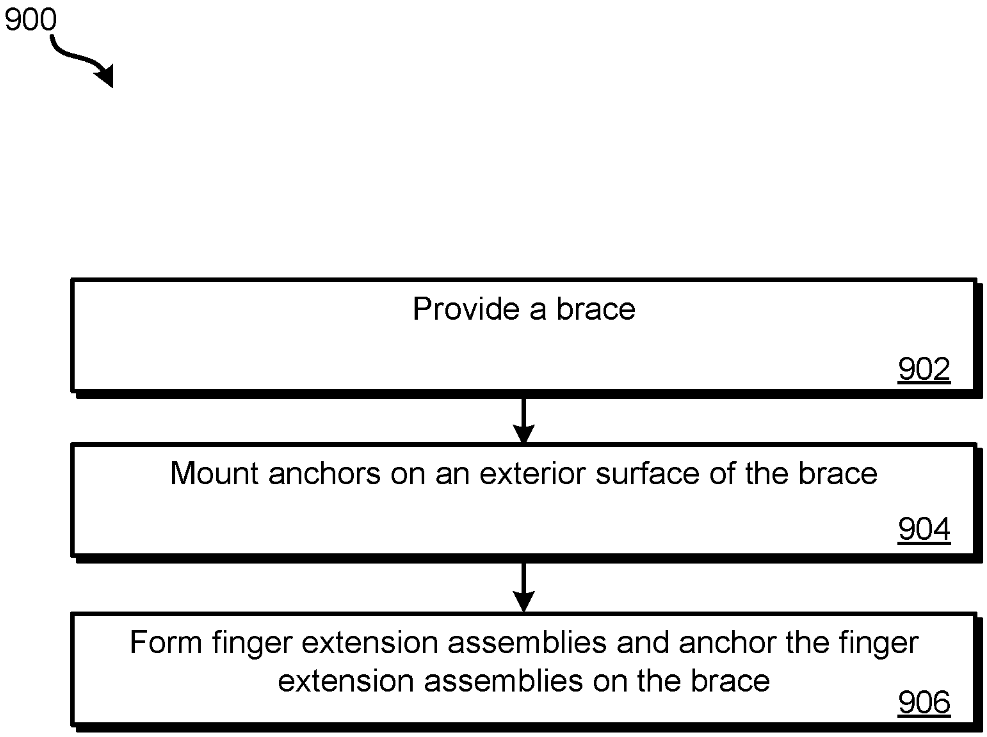
FIG. 9 is a flow diagram illustrating an example method of making/assembling the orthotic device according to various embodiments.

In yet another aspect, the present disclosure provides a method for the assembly of an orthotic device described herein. FIG. 9 is a flow diagram illustrating a method 900 for making/assembling an orthotic device according to various embodiments. Depending on the implementation, the method 900 may include additional, fewer, or alternative steps performed in various orders or in parallel. At 902, the brace 102 according to the present disclosure is provided. At 904, a plurality of anchors 206 are mounted to the exterior surface 144 of the brace 102. At 906, a plurality of finger extension assemblies 204 are formed and anchored on the brace 102. For example, one or more finger bands 212 are attached to the tensioning member 214 proximate the distal stopper 222 of the tensioning member 214. The tensioning member 214 is attached to the anchor 206 proximate to the proximal stopper 220 of the tensioning member 214 and thus is anchored on the brace 102. In some embodiments, the tensioning member 214 is further operated to extend through the vein 180 between the exterior surface 144 and the interior surface 146 of the major body 112. The tensioning member 214 is attached to the tension control member 208. In some embodiments, the support pad 170 is disposed into the pouch 168 of the brace 102.

The orthotic device may be disassembled, for example, in a reverse manner. The finger extension assemblies may be detached from the brace. The finger extension assemblies may be further disassembled bay removing the finger bands from the tensioning member. The support pad may be removed from the pouch of the brace. The brace, fabric cover, and tensioning member may be washable and reusable over time. The tensioning member and/or finger band may be replaceable.

Figure 10:
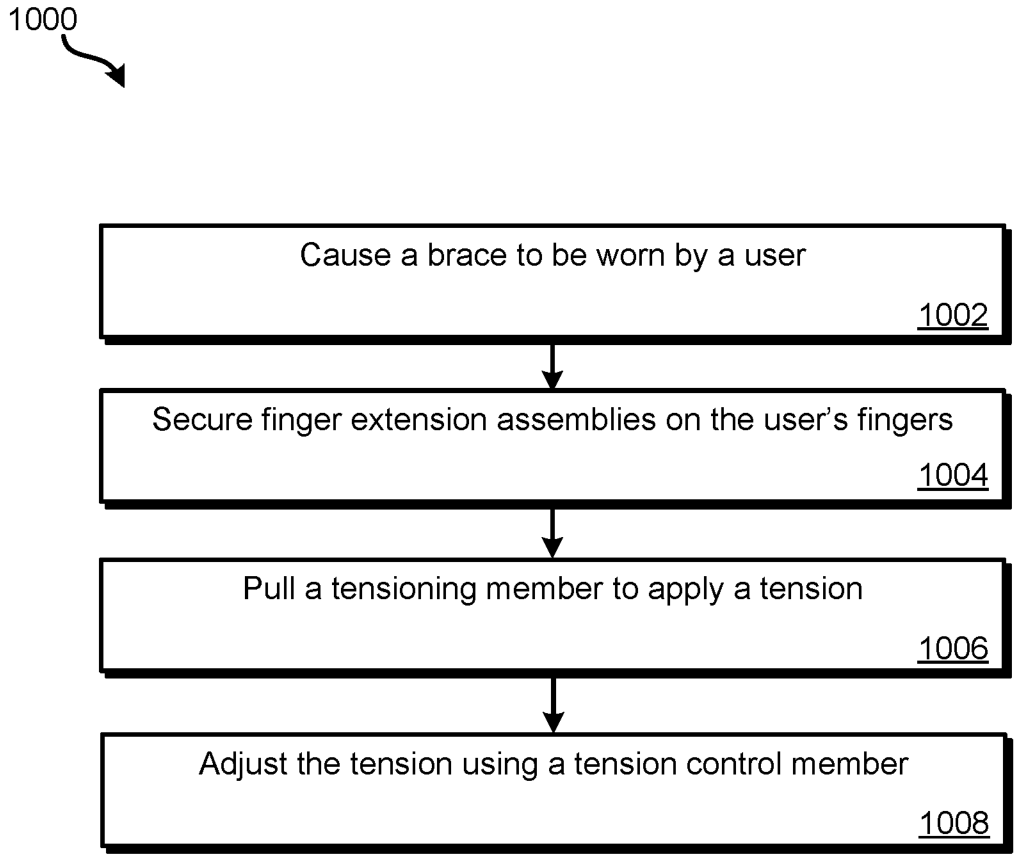
FIG. 10 is a flow diagram illustrating an example method of using the orthotic device according to various embodiments.

In a further aspect, the present disclosure provides a method for using an orthotic device described herein. FIG. 10 is a flow diagram illustrating a method 1000 for using an orthotic device according to various embodiments. Depending on the implementation, the method 1000 may include additional, fewer, or alternative steps performed in various orders or in parallel. At 1002, the brace 102 according to the present disclosure is worn by a user. For example, the major body 112 of the brace 102 is wrapped around the user's hand, wrist, and a portion of the forearm. The brace 102 is further secured on the user using the closure mechanism 116 (e.g., through the releasable fastener 160 such as a Velcro fastener. In some embodiments, the support pad 170 is disposed into the pouch 168 of the brace 102 to further support the wrist to allow the wrist to be secured out of flexion in an optimal position for functionality. The support pad 170 may be bent to a desired angle to comply with the desired position of the wrist and a desired position of the hand relative to the forearm. For example, in utilizing the support pad 170 to provide angular positioning of the wrist in a therapy program, a therapist or patient could determine a desirable angle or range of motion for a patient, or the support pad 170 could be pre-bended at an angle that could be subsequently movable and adjustable.

At 1004, a plurality of finger extension assemblies 204 are correspondingly secured on the fingers of the user. With respect to each finger extension assembly 204, at least one finger band 212 of the finger extension assembly 204 is placed and secured on the corresponding finger of the user. For example, a first finger band is placed and positioned on the intermediate phalange of the finger, and a second finger band is placed and positioned on the proximal phalange of the finger. The finger bands 212 may be fastened to the respective phalanges using the tightening element 218.

At 1006, the tensioning members 214 of the finger extension assemblies 204 are pulled toward the proximal edge of the brace to pull the user's fingers to a spread position. At 1008, the tension applied on the fingers is further controlled by the tension control member 208 to adjust the flexion/extension level and extend the corresponding phalange to a desired or optimal position relative to the hand.

The orthotic devices and methods described herein may be used in a treatment program, therapy program, or occupational program. In one particular example, the orthotic devices and methods may be used to treat a patient between the age of 5 to 10 and diagnosed with cerebral palsy (CP). The orthotic devices may be integrated into occupational therapy to take advantage of everyday activities as a means of promoting muscle relaxation and control. The orthotic device may be incorporated into a patient's home exercise program by their therapist to promote overlap between the completion of daily functional living tasks and therapeutic exercises. The orthotic device may enable the CP patients to obtain quicker results without having to spend more hours in physical or occupational therapy.

The orthotic device may be used in a therapy program to provide optimal positioning of the wrist and fingers out of the typical flexed position that is associated with spastic CP. The orthotic device utilizes variable tension bands to deliver personalized treatment to the patient and work to build up muscle fibers in the fingers and promote heightened muscle relaxation and control. As a result, the orthotic device serves to combat musculoskeletal deformities during childhood and allows for easier performance of common grasp and release tasks. The orthotic device not only provides support at essential points such as the wrist, the top of the palm, and the thumb in order to promote optimal positioning for function, and it also offers distal resistance therapy that can be adjusted according to the patient's specific and changing needs. Ultimately, the orthotic device will allow for easier performance of grasp and release tasks, which children with spastic CP traditionally struggle with. While the orthotic device allows patients to regain muscle control and relaxation more effectively, it does not compromise affordability and comfort in the process. The orthotic device is intended to be worn over the course of an entire day, and its relatively flexible and soft materials minimize the potential for discomfort.

Similarly, the materials and the assembly process for the orthotic device effectively limit the cost of this product. Wherever possible, components for the device may be taken from off-the-shelf, including the tensioning member and the tension control member. This contributes to minimizing the overall cost of the device and also allows for inexpensive and easy replacement of these components if they become damaged or worn out. The custom components of the device such as the finger bands and the releasable fasteners (e.g., Velcro fastener) are consumer-friendly, affordable, and manufacture-feasible.

In addition to the beneficial and qualitative uses already described herein, the orthotic device may also have quantitative features incorporated into it. For instance, the tensioning member may include a component for measuring the amount of tension or force being exerted by the tensioning member to cause extension of the fingers. In any case, the quantification of treatment may be used in therapy to identify the specific progress of the therapy.

The orthotic device described herein is intended to be simple to use and available to any patient or therapist. Therefore, it is envisioned that a kit containing the unconnected components described herein will be available to users or to therapists. Since some of the components may vary in size or length, depending on the needs of a given patient, it will be possible to select among possible parts included in the kit to meet individual requirements.

The devices, kits, and methods discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of exemplary configurations including implementations. However, configurations may be practiced without these specific details. This description provides example configurations only, and does not limit the scope, applicability, or configurations of the claims. Rather, the preceding description of the configurations will provide an enabling description for implementing described techniques. Various changes may be made in the function and arrangement of elements without departing from the spirit or scope of the disclosure.

As used herein and in the appended claims, the singular forms "a", "an", and "the" include plural references unless the context clearly dictates otherwise. Thus, for example, reference to "a user" includes a plurality of such users, and reference to "the finger band" includes reference to one or more finger bands and equivalents thereof, and so forth.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

From the foregoing, it will be seen that this disclosure is one well adapted to attain all the ends and objects hereinabove set forth together with other advantages derived from the structure. It will be understood that certain features and sub-combinations are of utility and may be employed without reference to other features and sub-combinations. This is contemplated by and is within the scope of the claims. Since many possible aspects may be made of the disclosure without departing from the scope thereof, it is to be understood that all matter herein set forth or shown in the accompanying drawings is to be interpreted as illustrative and non-limiting.

What is claimed is:

1. An orthotic device, comprising:
- a brace configured to be worn on a user's hand and wrist, the brace comprising:
  - a first portion configured to cover a top portion of the user's hand and wrist;
  - a second portion connected to the first portion configured to substantially align with the user's forearm, the second portion configured to cover a bottom portion of the user's hand and wrist;
  - a closure mechanism arranged and configured to form a closure between the first portion and the second portion and configured to secure the brace worn on the user's hand and wrist; and
  - a thumb support configured to receive and accommodate a portion of the user's thumb and configured to prevent thumb flexion of the user's thumb;
- a plurality of tensioning members;
- a plurality of cord lock, wherein:
  - each of the plurality of cord locks comprises a plunger, a housing, and a cap coupled to the plunger; and
  - each of the plurality of cord locks is directly attached to two or more of the plurality of tensioning members; and
- a plurality of finger extension assemblies configured to respectively correspond to the user's fingers, each one of the plurality of the finger extension assemblies further comprising:
  - an associated tensioning member of the plurality of cord locks anchored on an exterior surface of the brace, the associated tensioning member extending from a proximal stopper to a distal stopper;
  - at least one finger band configured to be worn on a phalange of the finger, the at least one finger band adapted to receive the phalange and comprising:
    - a tightening element configured to fasten the at least one finger band to the phalange; and
    - a connecting element configured to movably connect the at least one finger band to the associated tensioning member proximate to the distal stopper; and
  - an associated cord lock of the plurality of cord locks directly attached to the associated tensioning member proximate the proximal stopper, the associated cord lock configured to apply and control a tension on the at least one finger band connected to the associated tensioning member, wherein in response to the applied tension the associated tensioning member causes the user's finger to change from a flexion position to an extended position.

2. The orthotic device according to claim 1, further comprising:
- a semi-rigid and bendable support pad removably attached to an interior surface of the second portion, the support pad arranged and configured to cover the bottom portion of the user's wrist and configured to support the user's wrist at a desired angle between the user's hand and forearm.

3. The orthotic device according to claim 2, wherein the brace further comprises a pouch formed and located between the exterior surface and the interior surface of the second portion, the pouch extending from an open end at the interior surface to a closed end and configured to receive and accommodate the support pad inserted thereto.

4. The orthotic device according to claim 1, wherein the brace further comprises a plurality of anchors corresponding to the plurality of the finger extension assemblies, wherein each anchor is mounted on the exterior surface of the first portion, and the associated tensioning member of each finger extension assembly is anchored on the brace through the corresponding anchor.

5. The orthotic device according to claim 4, wherein the brace further comprises a flap attached to the brace, the flap configured to removably cover the plurality of anchors and the plurality of cord locks.

6. The orthotic device according to claim 1, wherein the closure mechanism comprises one or more releasable fasteners.

7. The orthotic device according to claim 6, wherein each of the releasable fasteners comprises a mated pair of a hook and loop strips.

8. The orthotic device according to claim 1, wherein each finger band further comprises a rigid portion adapted to cover a top portion of the phalange and a flexible portion adapted to cover a bottom portion of the phalange, wherein the rigid portion and the flexible portion form a closed loop, and the connecting element is located on the rigid portion.

9. The orthotic device according to claim 8, wherein the flexible portion comprises a foam strip tied to the rigid portion.

10. The orthotic device according to claim 1, wherein the brace further comprises a plurality of veins configured to respectively correspond to the user's fingers, wherein each vein is located between the exterior surface and an interior surface of the brace and extending from a first opening to a second opening in a direction configured to substantially align with a metacarpal of the user's hand, and wherein a portion of the associated tensioning member extends through the corresponding vein.

11. The orthotic device according to claim 1, wherein each finger extension assembly comprises two finger bands configured to be respectively worn on an intermediate phalange and a proximal phalange of the user's finger.

12. The orthotic device according to claim 1, wherein the brace is made of neoprene fabric.

13. The orthotic device according to claim 1, wherein each of the plurality of tensioning members is a cord.

14. The orthotic device according to claim 1, further comprising a fabric cover configured to removably cover the exterior surface of the brace.

15. A kit for an orthotic device, the kit comprising:

a brace configured to be worn on a user's hand and wrist, the brace comprising:

a first portion configured to cover a top portion of the user's hand and wrist;

a second portion connected to the first portion along a center line configured to substantially align with the user's forearm, the second portion configured to cover a bottom portion of the user's hand and wrist;

a closure mechanism arranged and configured to form a closure between the first portion and the second portion and configured to secure the brace worn on the user's hand and wrist; and a thumb support configured to receive and accommodate a portion of the user's thumb and configured to prevent thumb flexion of the user's thumb;

a plurality of cords extending from a proximal end and a distal end;

a plurality of cord locks, wherein:

each of the plurality of cord locks comprises a plunger, a housing, and a cap coupled to the plunger; and each of the plurality of cord locks is directly attached to more than one but fewer than all of the plurality of cords;

an associated finger band of a plurality of finger bands configured to be worn on a phalange of the user's finger, the associated finger band adapted to receive the phalange and comprising:

a tightening element configured to fasten the associated finger band to the phalange; and a connecting element removably connectable to an associated cord of the plurality of cords and movable along the associated cord;

an associated cord lock of the plurality of cord locks directly attachable to the associated cord proximate to the proximal end, the associated cord lock configured to apply and control a tension on the associated finger band connected to the associated cord lock and configured to cause a change of the user's finger from a flexion position to an extended position; and at least one anchor mountable on an exterior surface of the first portion of the brace, wherein the at least one anchor is configured to anchor the associated cord onto the brace.

16. The kit according to claim 15, further comprising:

a semi-rigid and bendable support pad removably attached to an interior surface of the second portion, the support pad arranged and configured to cover the bottom portion of the user's wrist and configured to support the user's wrist at a desired angle between the user's hand and forearm.

17. The kit according to claim 16, wherein the brace further comprises a pouch formed and located between the exterior surface and the interior surface of the second portion, the pouch extending from an open end at the interior surface to a closed end and configured to receive and accommodate the support pad to be inserted thereto.

18. The kit according to claim 15, wherein the brace further comprises at least one vein configured to respectively correspond to the user's fingers, wherein the at least one vein is located between the exterior surface and an interior surface of the brace and extending from a first opening to a second opening in a direction configured to substantially align with a metacarpal of the user's hand, and wherein the at least one vein is configured to accommodate a portion of the associated cord extending through the at least one vein.

19. The kit according to claim 15, wherein the brace further comprises a flap attached to the brace, the flap configured to removably cover the exterior surface of the first portion.

* * * * *